United States Patent [19]

Mason et al.

[11] Patent Number: 4,721,793

[45] Date of Patent: Jan. 26, 1988

[54] AZETIDINE-3-CARBOXYLIC ACID DERIVATIVES

[75] Inventors: Ronald F. Mason, Ashford; Paul H. Briner, Faversham, both of England

[73] Assignee: Shell Oil Company, Houston, Tex.

[21] Appl. No.: 756,430

[22] Filed: Jul. 18, 1985

[30] Foreign Application Priority Data

Jul. 26, 1984 [GB] United Kingdom ................. 8419084

[51] Int. Cl.$^4$ .......................................... C07D 205/04
[52] U.S. Cl. ................................................. 548/953
[58] Field of Search ................. 200/239 AR; 548/953

[56] References Cited

FOREIGN PATENT DOCUMENTS 1643 2/1979 European Pat. Off. .
114706 8/1984 European Pat. Off. ...... 260/239 AR

OTHER PUBLICATIONS

K. Kumoto et al., Chem. Abstracts, vol. 89 (1978), entry 197344g.
March, ed., Advanced Organic Chemistry, 2nd ed., McGraw-Hill (1977), pp. 809–810 and 813–814.
Sandler et al., Organic Functional Group Preparations, vol. III, Academic Press (1972), pp. 268–273.
Spiegel, Chem. Berichte, vol. 51 (1918), pp. 296–298.

*Primary Examiner*—Donald G. Daus
*Assistant Examiner*—William A. Teoli, Jr.

[57] ABSTRACT

The novel ester, N-benzylazetidine-3-carboxylic acid methyl ester and its use in the preparation of the corresponding free acid by a process which comprises reacting N-benzyl-3-cyanozetidine with methanol and hydrolyzing the resulting methyl ester with hot water.

1 Claim, No Drawings

AZETIDINE-3-CARBOXYLIC ACID DERIVATIVES

BACKGROUND TO THE INVENTION

European Patent Application Publication No. 29265 discloses that azetidine-3-carboxylic acid and related compounds are useful as plant hybridizing agents, based on their ability to produce male sterility in plants. Azetidine-3-carboxylic acid can be prepared from 1-benzhydrylazetidin-3-ol, which is prepared by the reaction of epichlorohydrin with benzhydrylamine: A. G. Anderson, Jr. and R. Lok, Journal of Organic Chemistry, 1972, volume 37, pages 3953-5. According to that article, the alcohol is converted to the mesylate ester, which is converted to the nitrile, which is converted to the carboxy acid, then the protective benzhydryl moiety is removed by hydrogenation.

However, the introduction of a benzhydryl group is very inconvenient for an economically practicable synthesis route, since the size of that group greatly increases the bulk of material to be processed, only to be removed once its protective function is no longer required. It would be economically very desirable to use a protective group less bulky than the benzhydryl group, and applicants have found that azetidine-3-carboxylic acid can be prepared by heating an aqueous mixture of N-benzyl-3-cyanoazetidine and barium hydroxide and then treating the mixture with carbon dioxide, to form N-benzylazetidine-3-carboxylic acid, then removing the protective benzyl moiety by hydrogenation.

However, preparation of azetidine-3-carboxylic acid from N-benzyl-3-cyano azetidine involves practical difficulties of compound separation/extraction as a consequence of its high water solubility—which problems do not occur when using the benzhydryl analogue, since the analogue is essentially insoluble in water and therefore is readily freed from inorganic contaminants/by-products. Applicants have therefore sought a practically convenient route for hydrolyzing N-benzyl-3-cyanoazetidine to N-benzyl-3-carboxylic acid and have surprisingly discovered that conversion via the methyl ester affords a unique combination of process advantages, namely effective separation of the organic ester product from an aqueous reaction medium and the inorganic impurities contained therein, and also the ability of the methyl ester to undergo hydrolysis with hot water.

DESCRIPTION OF THE INVENTION

This invention accordingly comprises the compound N-benzylazetidine-3-carboxylic acid methyl ester, of the formula

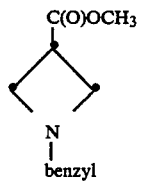
(I)

and a process for preparing azetidine-3-carboxylic acid from it. The invention also includes a process for preparing N-benzylazetidine-3-carboxylic acid, of the formula

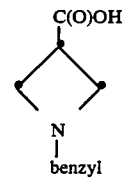
(II)

which comprises forming N-benzylazetidine-3-carboxylic acid methyl ester, by treating N-benzyl-3-cyanoazetidine with methanol at an elevated temperature in the presence of a strong acid, adding water to the reaction mixture, basifying the mixture, extracting the methyl ester from the aqueous mixture with a water immiscible organic solvent, removing the organic solvent, and hydrolyzing the methyl ester with water at an elevated temperature.

The reaction of the cyano compound with methanol is effected in the presence of a strong acid, which suitably is an inorganic acid such as sulfuric acid or hydrogen chloride, with concentrated sulfuric acid usually being preferred, and at an elevated temperature, which is preferably at least 50° C., suitably as high as 90°-100° C., and conveniently at the reflux temperature of the mixture. The methanol and strong acid are desirably utilized in substantially equal volumes; lower amounts of acid adversely affect the reaction rate, while lower amounts of methanol lead to less efficient reflux control and an inconveniently viscous reaction mixture.

After the reaction is complete, the reaction mixture is diluted with water, conveniently combined with cooling by pouring the mixture into a relatively large volume of ice or ice/water. This aqueous mixture is then basified, suitably by the addition of ammonia, and the methyl ester intermediate product is extracted with a water-immiscible organic solvent. Any such solvent having the necessary physical properties and chemical inertness may be used, methylene chloride and paraffinic hydrocarbons, particularly those boiling in the range of 60° C. to 80° C., having been found convenient in practice. The solvent is then removed, suitably by evaporation.

The N-benzylazetidine-3-carboxylic acid methyl ester product is then hydrolyzed by treatment with hot, preferably boiling, water. The completion of hydrolysis is usually marked by the transformation of the initial oily, two-phase system into a homogeneous system, and normally requires about one hour. The water may be removed from the final mixture by evaporation, and the desired product, N-benzylazetidine-3-carboxylic acid, is readily isolated as a solid. Alternatively, if it is desired to proceed with the ultimate preparation of the deprotected azetidine-3-carboxylic acid, the major part of the water may be removed (e.g., by evaporation), and the crude, wet N-benzyl acid subjected to a conventional deprotection treatment, e.g., palladium catalyzed hydrogenolysis.

The precursor N-benzyl-3-cyanoazetidine may be prepared by appropriate adaptations of known synthetic procedures. A convenient synthesis route to that compound is described in applicants' European Application No. 0169603, namely by reacting the corresponding 3-hydroxyazetidine with an alkylsulfonyl halide, e.g., mesyl chloride, followed by treatment with an alkali metal cyanide in the presence of a phase transfer catalyst such as "Adogen" 464.

As mentioned above, the N-benzylazetidine-3-carboxylic acid methyl ester of formula I, and the corresponding free acid of formula II, are useful intermediates. Thus, they may be converted by known procedures, for example by hydrogenolysis, to azetidine-3-carboxylic acid.

The invention is illustrated in the following Examples. In each case, the identity of the product was confirmed by appropriate chemical and spectral analyses.

EXAMPLE 1

(a) 60 ml of concentrated sulfuric acid (sp. gr. 1.84) was added over 15 minutes to a stirred mixture of 17 g of N-benzyl-3-cyanoazetidine and 60 ml of methanol at room temperature. The reaction was exothermic and the temperature was held in the range 50°–55° C. After 2 hours at 80°, the reaction mixture was drowned in 400 g of ice, basified with 120 ml of ammonia (0.88 sp. gr.), and extracted with methylene chloride. The extract was washed with water and stripped in a rotary evaporator. The residue was distilled in a Vigreaux column to give N-benzylazetidine-3-carboxylic acid methyl ester (1A), b.p.: 92°–95° C. at 0.2 mm Torr.

(b) 1.5 g of 1A was mixed with 25 ml of distilled water and a few boiling chips and boiled under a nitrogen blanket. After 40 minutes reflux, the initial oily two phase system became homogenous. The water was stripped on a rotary evaporator and the product readily crystallized. After drying in a vacuum oven at 60°, N-benzylazetidine-3-carboxylic acid (1), m.p.: 152°–154°, was obtained.

EXAMPLE 2

The procedure of Example 1A) was repeated, except that the post-basifying extraction was carried out with a commercial mixture of $C_5$ to $C_8$ parafinnic hydrocarbons boiling between 60° and 80° C. This produced the desired methyl ester in a yield of 82%. Wiped film distillation (168° C., 5 Torr.) yielded this product in 91% purity.

EXAMPLE 3

Use of N-benzylazetidine-3-carboxylic acid to prepare azetidine-3-carboxylic acid 0.5 g of 1 in 15 ml of methanol was hydrogenated in the presence of a 5% palladium on carbon catalyst at room temperature. The catalyst was filtered off and the solvent was removed from the filtrate under reduced pressure to give azetidine-3-carboxylic acid in 90% yield.

EXAMPLE 3

(Comparative)

(a) The ethyl and isopropyl esters of N-benzylazetidine-3-carboxylic acid were prepared following procedures similar to those described in Example 1, but replacing the methanol with, respectively, ethanol and isopropanol. In the latter case, the yield was low when using concentrated sulfuric acid as the strong acid, but was increased to 70% by replacing that acid with gaseous hydrogen chloride.

(b) Each of the esters prepared in Example 3A was hydrolyzed by refluxing one gram of the ester in ten milliliters of distilled water; the hydrolysis proceeded quite differently from that of the methyl ester. The methyl ester gave a clear solution (the criterion for complete conversion) in 37–40 minutes, whilst the ethyl ester requires 6 hours and the isopropyl ester 24–40 hours. Thus, the hydrolysis time (using boiling water) for the ethyl and isopropyl esters is inconveniently long for a commercial scale of synthesis, whereas the methyl ester hydrolysis very rapidly under those same, convenient conditions.

We claim:

1. N-Benzylazetidine-3-carboxylic acid methyl ester.

* * * * *